United States Patent [19]
Ahonen

[11] Patent Number: 5,584,386
[45] Date of Patent: Dec. 17, 1996

[54] CONTAINER FOR SAFELY STORING AND DISINFECTING USED MEDICAL INSTRUMENTS

[76] Inventor: Peggy S. Ahonen, 4196 Bullord Rd., Hartland, Mich. 48353

[21] Appl. No.: 416,355

[22] Filed: Apr. 4, 1995

[51] Int. Cl.⁶ .................................................. B65D 81/18
[52] U.S. Cl. .......................... 206/210; 206/365; 206/366; 206/370
[58] Field of Search .................................... 206/63.5, 210, 206/365, 366, 370; 422/292, 300, 310

[56] References Cited

U.S. PATENT DOCUMENTS

| | | | |
|---|---|---|---|
| 3,876,067 | 4/1975 | Schwarz . | |
| 4,380,292 | 4/1983 | Cramer | 206/63.5 |
| 4,816,307 | 3/1989 | Honeycutt | 206/366 |
| 4,845,923 | 7/1989 | Donovan | 206/365 |
| 4,890,734 | 1/1990 | Gach . | |
| 4,927,076 | 5/1990 | Simpson . | |
| 4,936,449 | 6/1990 | Conard et al. | 206/366 |
| 4,959,220 | 9/1990 | Yamamoto et al. . | |
| 5,020,665 | 6/1991 | Bruno | 206/366 |
| 5,038,929 | 8/1991 | Kubofcik . | |
| 5,038,938 | 8/1991 | Berndt . | |
| 5,084,027 | 1/1992 | Bernard | 206/365 |
| 5,172,808 | 12/1992 | Bruno | 206/366 |
| 5,201,418 | 4/1993 | Hanlon | 206/366 |
| 5,230,428 | 7/1993 | McShane | 206/365 |
| 5,249,679 | 10/1993 | Dondlinger | 206/365 |
| 5,265,724 | 11/1993 | Dondlinger . | |
| 5,271,892 | 12/1993 | Hanson et al. . | |
| 5,325,965 | 7/1994 | Kelley . | |
| 5,372,252 | 12/1994 | Alexander . | |
| 5,385,105 | 1/1995 | Withers, Jr. et al. . | |
| 5,411,193 | 5/1995 | Culp . | |
| 5,427,234 | 6/1995 | Upchurch | 206/365 |

*Primary Examiner*—Jimmy G. Foster
*Attorney, Agent, or Firm*—Harness, Dickey & Pierce, P.L.C.

[57] ABSTRACT

A container for holding and disinfecting invasive medical instruments, such as hypodermic needles and scalpels. The container includes a cylindrical side wall and a bottom wall defining an enclosure with an open upper end. A layer of sand is placed in the container to give the container stability. An open cell foam layer saturated with a disinfecting solution is placed on the sand layer to provide a disinfecting medium. A sealing membrane is positioned over the foam layer to prevent the fluid in the foam layer from escaping from the container. A fibrous cork layer is positioned on the membrane at the open end of the container. The medical instruments are inserted into the container through the cork layer and the sealing membrane such that a contaminated end of the instrument is positioned within the foam layer. The disinfecting fluid in the foam layer kills various viruses and germs, and the cork layer holds the instrument in place.

20 Claims, 1 Drawing Sheet

CONTAINER FOR SAFELY STORING AND DISINFECTING USED MEDICAL INSTRUMENTS

BACKGROUND OF THE INVENTION

1. Field of the Invention

This invention relates generally to a container for storing and disinfecting used medical instruments and, more particularly, to a container for storing and disinfecting used medical instruments, such as hypodermic needles and scalpels, in which the contaminated portion of the instrument is inserted through a stabilizing medium that rigidly holds the instrument and into a disinfecting medium for disinfecting the instrument.

2. Discussion of the Related Art

In the health care environment, prevention of the spread of germs, blood born pathogens, and the like is of a foremost interest. As is well understood in the art, the AIDS and hepatitis B viruses, certain germs, as well as other contaminants, can be extremely dangerous and contagious, and create a vulnerable environment for both the health care worker and the patient. It is very important that after the use of certain invasive medical instruments, the instruments be stored in a suitable location so as to prevent injury and the spread of viruses, germs and contaminants to the health care workers and patients. For example, after a health care worker has injected a patient with a medical solution by means of a disposable hypodermic needle, it is important to immediately store the used hypodermic needle in a secure location for subsequent disposal so as to reduce the chance that the health care worker will be injured by the sharp point of the needle, or be exposed to contamination on the needle, such as from certain blood born pathogens. The AIDS and hepatitis B viruses are sometimes transmitted by puncture wounds from hypodermic needles. Likewise, other medical instruments, such as scalpels, need to also be stored in a safe place following use to prevent injury and the spread of germs and viruses before sterilization and subsequent reuse.

Many types of containers are known in the prior art that are used to temporarily store hypodermic needles and the like after use for subsequent disposal, or reuse. Some of these containers include disinfecting mediums, such as bleach, that disinfect the instruments to prevent the spread of germs and viruses. However, although there are many types of such containers, there is still room for improvement in the design and use of these containers to further reduce the chance that germs and viruses will be spread to health care workers after use of the instruments, or that the health care worker will be injured by the instruments.

It is an object of the present invention to provide a container that allows for the storage and disinfecting of hypodermic needles and invasive medical instruments subsequent to their use.

SUMMARY OF THE INVENTION

In accordance with the teaching of the present invention, a container for storing and disinfecting hypodermic needles and/or other invasive medical instruments, after use is disclosed. The container includes side walls and a bottom wall made, for example, of a robust and inexpensive plastic, that define an enclosure having an open upper end. A weighting material is placed in the container adjacent to the bottom wall to lower the center of gravity of the container, and prevent it from being readily tipped. A porous layer, such as an open cell foam, is placed in the container on the weighting material and is saturated with a disinfecting solution, such as bleach. A thin, sealing membrane is attached to the inside of the container above the porous layer to prevent the disinfecting solution from escaping from the container. A fibrous layer, such as a cork layer, is positioned in the container above the membrane, adjacent the open end, and acts to support the medical instruments while in the container. In use, the sharp tip or edge of the medical instrument is forced through the fibrous layer and the sealing membrane into the porous layer where it is disinfected. The container can be placed in a suitable base to provide additional support if desirable.

Additional objects, advantages and features of the present invention will become apparent from the following description and appended claims, taken in conjunction with the accompanying drawings.

DETAILED DESCRIPTION OF THE PREFERRED EMBODIMENTS

The following description of the preferred embodiments directed to a container for storing and disinfecting hypodermic needles and other invasive medical instruments is merely exemplary in nature and is in way intended to limit the invention or its applications or uses.

Figure 1:
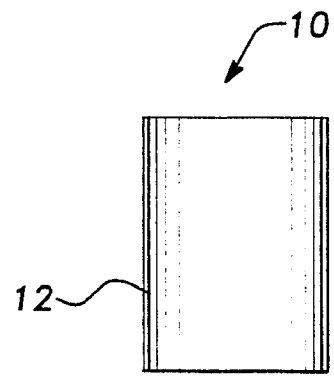
FIG. 1 is a side view of a container for holding medical instruments, according to an embodiment of the present invention.
Figure 2:
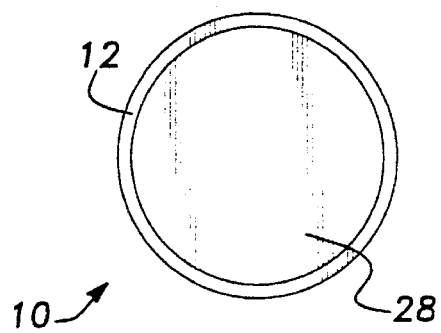
FIG. 2 is a top view of the container of FIG. 1.
Figure 3:
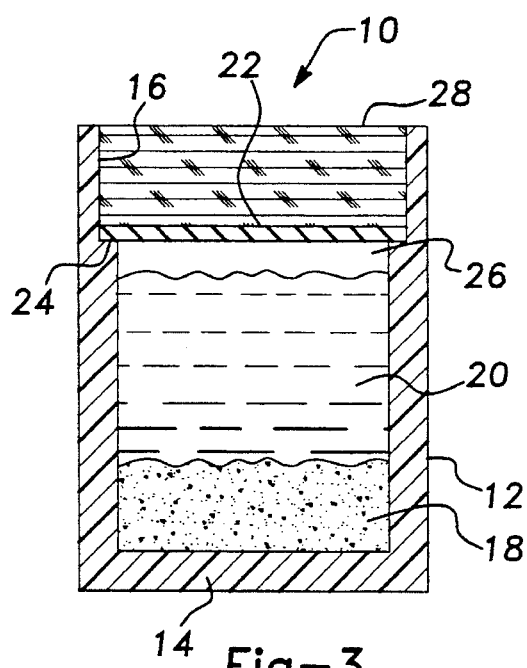
FIG. 3 is a cross-sectional side view of the container of FIG. 1.

FIGS. 1–3 show various views of a container 10 for holding, storing and/or disinfecting various invasive medical instruments, such as hypodermic needles and scalpels. The container 10 includes a cylindrical side wall 12 and a bottom wall 14 that define an enclosure having an open upper end 16 to allow for the insertion of the medical instruments into the container 10 in the manner as described below. The side wall 12 and the bottom wall 14 are made of a suitable plastic, such as PVC or polystyrene, so as to be inexpensive, easily manufactured by injection molding and the like, and durable against breaking and punctures.

A weighting material 18 is placed through the open end 16 of the container 10 to rest on an inside surface of the bottom wall 14 so as to stabilize the container 10 to help prevent it from tipping and moving. In one embodiment, the weighting material 18 is sand, but can be any suitably heavy material known in the art. A layer 20 of a foam material is positioned in the container on the weighting material 18 and acts to hold the weighting material 18 in place. In one embodiment, the foam layer 20 is an open cell foam that is saturated with a disinfecting fluid, such as a chlorine and water combination. A thin sealing membrane 22 is secured within the container 10 above the foam layer 20 by a suitable securing device, such as glue or the like, on a circumferential shoulder 24 formed on the inside surface of the side wall 12. In one embodiment, the thin sealing membrane 22 is made of a vinyl or rubber material that prevents the disinfecting fluid within the foam layer 20 from escaping from the container 10. An air space 26 is left between the foam layer 20 and the sealing membrane 22 to accommodate for expansion and contraction of the foam layer 20. A fibrous layer 28 is located within the container 10 adjacent to the open end 16, and rests on the membrane 22 opposite to the foam layer 20. The fibrous layer 28 is secured to the inside of the container 10 by a suitable glue, such as a silicon glue, to withstand the forces from inserting the medical instruments into the container 10. In one example, the fibrous layer 28 is cork that is very porous and allows air to circulate within the fibrous layer 28.

When a health care worker is finished using a hypodermic needle, scalpel, or other invasive medical instrument (not shown), and wishes to store the instrument to be subsequently discarded, cleaned and/or reused, the worker will insert the pointed or sharp end of the medical instrument into the container 10 by inserting it through the fibrous layer 28 and the sealing membrane 22 so that the dirty or contaminated end of the needle or blade is positioned within the foam layer 20. Because the fibrous layer 28 is very rigid, the medical instrument will be held securely in place in the event that the container 10 is bumped or aggressively moved in some manner. Additionally, the fibrous and porous quality of the layer 28 allows air to enter the layer 28, and has the affect of separating the AIDS virus from its protective cell wall in a way that does not support the life of the AIDS virus. In other words, the natural fiber of the cork will separate the AIDS virus from its protein sheath causing it to dehydrate. Thus, the AIDS virus will not survive in the layer 28. The layer 28 can be soaked with any type of solution or medication that would kill microorganisms, pathogens, or viruses known to cause communicable diseases. Likewise, the disinfecting fluid saturating the foam layer 20 will disinfect the contaminated portion of the medical instrument. The disinfecting fluid is prevented from splashing out of the container 10 by the membrane 22 and the layer 28.

Figure 4:
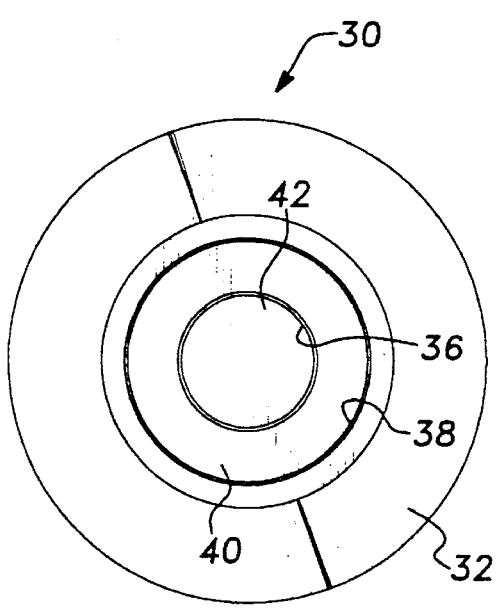
FIG. 4 is a top view of a base member for supporting the container of FIG. 1.
Figure 5:
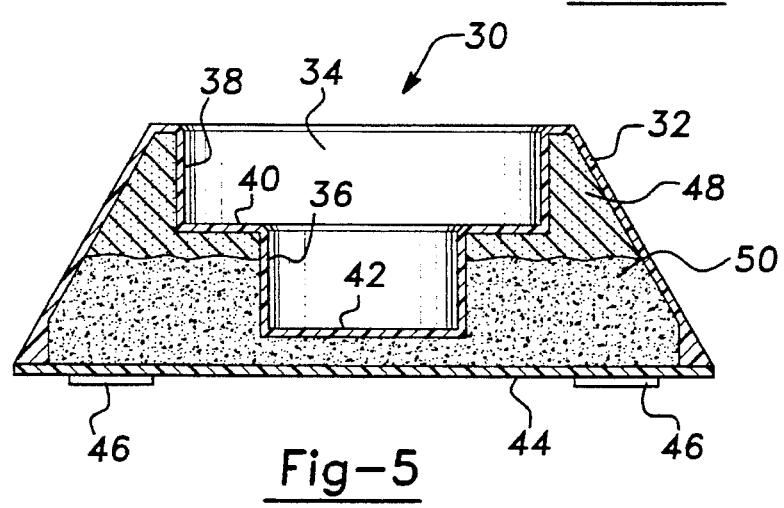
FIG. 5 is a cross-sectional side view of the base member of FIG. 4.

FIGS. 4 and 5 show two various views of a base member 30 that is applicable to support the container 10 in a more rigid or stable manner to further prevent the container 10 from being tipped or knocked over. The base member 30 includes a cone shaped outer side wall 32, an internal open area 34 defined by cylindrical internal walls 36 and 38 defining a shoulder 40 therebetween, and an internal bottom wall 42. The container 10 is inserted into the open area 34 such that the bottom wall 14 of the container 10 rests on the shoulder 40 or the internal bottom wall 42, depending on the container size. An external bottom wall 44 is secured to the outer side wall 32, as shown. In one embodiment, all the walls of the base member 30 are made of a suitable plastic, such as PVC or polystyrene, The bottom wall 44 is attached to the side wall 32 by a suitable glue. Skid resistant pads 46 are secured to a bottom surface of the bottom wall 44 to help secure the base member 30 to a table, counter, etc. In embodiment, the skid resistant pads 46 can be a soft rubber or vinyl material.

Prior to the bottom wall 44 being attached to the side wall 32, the base member 30 is filled with a foam rubber material 48 and a sand 50. The sand 50 is positioned on the bottom wall 44, and provides a lower center of gravity to give the base member 30 further stability. The foam rubber material 48 fills the remaining portion of the base member 30 to hold the sand 50 in place. Of course, other weighting materials can be used in place of the sand 50.

As discussed above, the container 10 provides a very stringent infection control device designed to totally protect the health care worker. The container 10 provides a safe receptacle for contaminated needles and instruments, while simultaneously disinfecting the instruments. The fibrous cork layer 28 not only holds the instruments in a rigid configuration such that they are not easily removable from the container 10, but also allows air to enter the fibrous cork layer 28 to prevent extended life of many viruses, but also help prevent the disinfecting fluid in the foam layer 20 from being released from the container 10. The container 10 can be a disposable unit that can be thrown away with disposable instruments, and the base member 30 can be reusable with other disposable containers 10. The natural fiber of the cork in the fibrous layer 28 will separate the AIDS virus from its protein outer cell wall that supports its life, causing it to dehydrate.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

I claim:

1. A container assembly for holding and disinfecting medical instruments, said container assembly comprising:

a side wall and a bottom wall defining an enclosure housing with an open upper end, said side wall having an intermediate shoulder below said open upper end;

a disinfecting medium positioned within the enclosure housing, said disinfecting medium including a disinfecting fluid;

a sealing medium positioned within the enclosure housing, having edges resting on said shoulder at an opposite side of the disinfecting medium from the bottom wall, said sealing medium preventing the disinfecting fluid in the disinfecting medium from escaping through the open end of the enclosure housing; and a fibrous, porous holding medium positioned within the enclosure housing and substantially closing open end, said holding medium being adjacent to a side of the sealing medium opposite to the disinfecting medium, wherein the medical instruments are held in the enclosure housing by the holding medium in a way that a contaminated portion of the instruments extend into the disinfecting medium through the sealing medium.

2. The container assembly according to claim 1 wherein the disinfecting medium includes an open cell foam material saturated with the disinfecting fluid.

3. The container assembly according to claim 1 wherein the disinfecting fluid is a mixture of chlorine bleach and water.

4. The container assembly according to claim 1 wherein the sealing medium is a sealing membrane made of a material selected from the group consisting of vinyl and rubber.

5. The container assembly according to claim 1 wherein the fibrous, porous holding medium is a cork.

6. The container assembly according to claim 1 wherein the fibrous, porous holding medium encapsulates a material fatal to microorganisms, pathogens and viruses.

7. The container assembly according to claim 1 further comprising a weighting material positioned within the enclosure housing on the bottom wall such that the disinfecting medium is positioned on the weighting material, said weighting material giving the container assembly stability.

8. The container assembly according to claim 7 wherein the weighting material is sand.

9. The container assembly according to claim 1 wherein the side wall and the bottom wall define a cylindrical enclosure housing and wherein the side wall and the bottom wall are made of a puncture resistant plastic.

10. The container assembly according to claim 1 further comprising a base member, said base member including a bottom wall, an outside wall and an inside wall, said inside wall including an internal resting surface, said bottom wall of said enclosure housing being configured to rest on the resting surface in the base member.

11. The container assembly according to claim 10 wherein the base member includes a weighting material to give the base member support.

12. A container assembly for holding and disinfecting a medical instrument, said container assembly comprising:

- a side wall and a bottom wall defining an enclosure housing with an open upper end;
- a weighting layer positioned within the enclosure housing on the bottom wall, said weighting layer giving the container assembly stability;
- a foam layer positioned within the enclosure housing on the weighting layer, said foam layer being saturated with a disinfecting fluid, said foam layer holding the weighting layer in place;
- a thin sealing layer secured to the enclosure housing adjacent to the foam layer and opposite to the weighting layer, said sealing layer preventing the disinfecting fluid from escaping through the open end of the enclosure housing; and
- a fibrous, porous holding layer positioned within the enclosure housing at the open end adjacent to a side of the sealing layer opposite to the foam layer, wherein the medical instrument is held in the enclosure housing by the holding layer such that a contaminated portion of the instrument extends into the foam layer through the sealing layer.

13. The container assembly according to claim 12 wherein the sealing layer is a sealing membrane made of a material selected from the group consisting of vinyl and rubber.

14. The container assembly according to claim 12 wherein the holding layer is made of a cork material.

15. The container assembly according to claim 12 wherein the weighting layer is sand.

16. The container assembly according to claim 12 wherein the disinfecting fluid is a mixture of chlorine bleach and water.

17. The container assembly according to claim 12 wherein the holding layer capsulates a material fatal to microorganisms, pathogens, and viruses.

18. The container assembly according to claim 12 wherein the side wall and the bottom wall define a cylindrical enclosure housing and wherein the side wall and the bottom wall are made of a puncture resistant plastic.

19. A container assembly for holding and disinfecting a medical instrument, said container assembly comprising:

- a cylindrical plastic side wall and a plastic bottom wall defining an enclosure housing with an open upper end;
- a sand layer positioned within the enclosure housing on the bottom wall, said sand layer giving the container assembly stability;
- an open cell foam layer positioned within the enclosure housing on the sand layer, said open cell foam layer being saturated with a disinfecting fluid, said foam layer holding the sand layer in place;
- a sealing membrane secured to the enclosure housing adjacent to the foam layer and opposite to the sand layer, said sealing membrane preventing the disinfecting fluid from escaping through the open end of the enclosure housing; and
- a cork layer positioned within the enclosure housing at the open end adjacent to a side of the sealing membrane opposite to the foam layer, wherein the medical instrument is held in the enclosure housing by the cork layer such that a contaminate portion of the instrument extends into the foam layer through the sealing membrane to be sterilized.

20. The container assembly according to claim 19 wherein the cork layer encapsulates a material fatal to microorganisms, pathogens and viruses.

* * * * *